(12) United States Patent
Burko

(10) Patent No.: US 6,599,282 B2
(45) Date of Patent: Jul. 29, 2003

(54) INTRAVENOUS SET FLOW VOLUMETRIC MEASUREMENT DEVICE

(76) Inventor: Zeev Burko, 17 Rechov Szold, Ramat Hasharon 47225 (IL)

(*) Notice: Subject to any disclaimer, the term of this patent is extended or adjusted under 35 U.S.C. 154(b) by 3 days.

(21) Appl. No.: 09/945,786

(22) Filed: Sep. 5, 2001

(65) Prior Publication Data

US 2003/0045840 A1 Mar. 6, 2003

(51) Int. Cl.[7] .............................................. A61M 31/00
(52) U.S. Cl. ................. 604/507; 604/253; 128/DIG. 13
(58) Field of Search ........................... 604/65, 66, 246, 604/251, 252, 253, 254, 255, 256, 500, 507, 508, 28, 30, 48; 128/898, DIG. 13

(56) References Cited

U.S. PATENT DOCUMENTS

| | | | |
|---|---|---|---|
| 3,450,153 A | * 6/1969 | Hildebrandt et al. ........ 604/253 |
| 4,504,263 A | 3/1985 | Steuer et al. | |
| 4,525,163 A | 6/1985 | Slavik et al. | |
| 4,681,563 A | 7/1987 | Deckert et al. | |
| 4,797,655 A | 1/1989 | Orndal et al. | |
| 4,820,281 A | * 4/1989 | Lawler, Jr. ................. 604/253 |
| 4,834,104 A | 5/1989 | Kreinick et al. | |
| 4,936,828 A | 6/1990 | Chiang | |
| 5,045,069 A | * 9/1991 | Imparato ..................... 604/253 |
| 5,098,409 A | 3/1992 | Stock | |
| 5,154,704 A | 10/1992 | Archibald | |
| 5,177,993 A | 1/1993 | Beckman et al. | |
| 5,211,626 A | 5/1993 | Frank et al. | |
| 5,377,101 A | 12/1994 | Rollema | |
| 5,445,622 A | 8/1995 | Brown | |
| 5,563,584 A | 10/1996 | Rader et al. | |
| 5,588,963 A | 12/1996 | Roelofs | |
| 6,083,206 A | 7/2000 | Molko | |
| 6,110,153 A | 8/2000 | Davis et al. | |
| 6,149,631 A | 11/2000 | Haydel, Jr. | |
| 6,159,186 A | 12/2000 | Wickham et al. | |
| 6,213,354 B1 | 4/2001 | Kay | |

* cited by examiner

Primary Examiner—Manuel Mendez
Assistant Examiner—Mark K. Han
(74) Attorney, Agent, or Firm—Mark M. Friedman

(57) ABSTRACT

A method and device for volumetric measurement of a drop of fluid administered in a gravity intravenous set. Radiation, preferable infrared light is passed through from the exterior of the drip chamber of the intravenous set and is detected and quantified by a receiver on the other exterior side of the chamber. The radiation passing through the chamber when a drop is not passing through the radiation path is taken as the background radiation level. When a drop passes through the chamber, a loss in radiation passing through the receiver occurs. This relative loss is converted into volume with the aid of a lookup table.

7 Claims, 3 Drawing Sheets

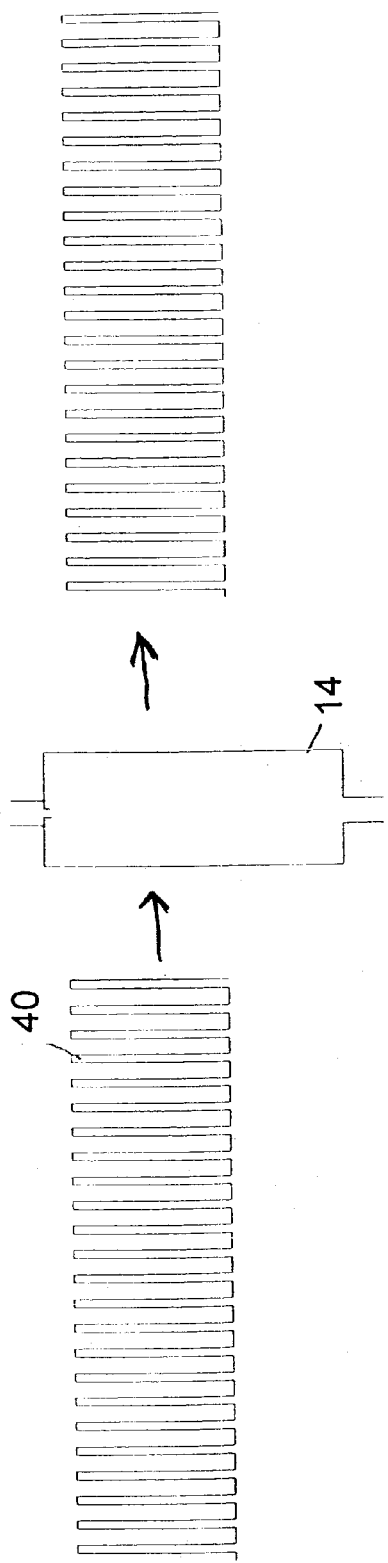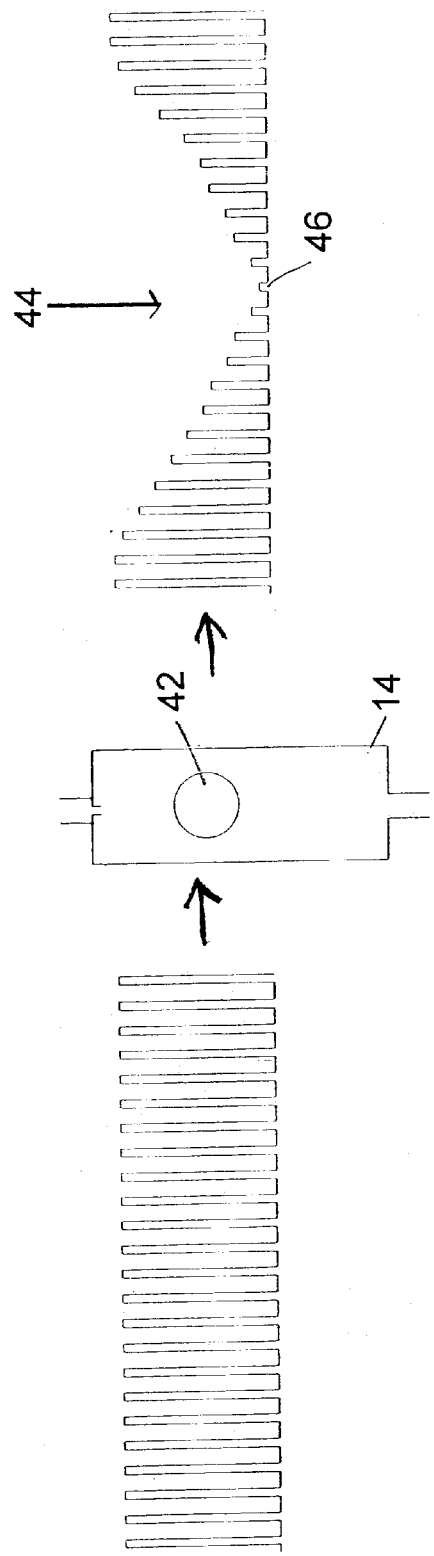

INTRAVENOUS SET FLOW VOLUMETRIC MEASUREMENT DEVICE

FIELD AND BACKGROUND OF THE INVENTION

The present invention relates to the flow of fluids into a patient's blood stream and, more particularly, to a system and method for the volumetric measurement of fluids administered in any standard gravity intravenous infusion set.

The intravenous infusion of fluids into a patient's bloodstream is a common medical procedure. Fluids that are typically administered intravenously include glucose and saline solutions, drugs, and blood. Intravenous (IV) systems generally comprise a reservoir, a drip chamber, a feed tube, and an IV needle. The reservoir, also called an IV bag, holds a quantity of the fluid to be infused. The reservoir is coupled to a dripper by means of a feed tube. The dripper, in turn, is coupled by the feed tube to the hollow IV needle, which is injected into a vein of the patient. The fluid in the reservoir drips through the needle and into the bloodstream, with the drip rate being controlled by the dripper.

In the past, two major approaches have been used to control the rate at which fluids are administered intravenously. The first approach is to use a conventional drip chamber which is manually controlled to adjust the drop rate through the drip chamber until the drops fall at a predetermined rate. This approach brings with it the advantage of simplicity in that only gravitational forces are needed to maintain the flow of fluids through the drip chamber.

However, manually controlled drip chambers are not satisfactory for all applications, for such drip chambers can permit fluid flow rate inaccuracies above or below the requested flow rate. These inaccuracies are due to the fact that the size of individual drops passing through the drip chamber can vary from set to set, the flow rate with which the fluid passes through the drip chamber, fluid pressure, and vibrational influences on the drip chamber. Furthermore, unless the drip chamber is carefully made to exacting tolerances, the drop volume may vary from one drip chamber to the next and definitely from one type of set to the next type. This means that a drop rate appropriate for a preselected fluid flow rate with a first drip chamber is not necessarily appropriate for a second drip chamber. Moreover, because of cold flow of tubing used in conjunction with conventional pinch clamps, a conventional, manually controlled drip chamber which is operating at a desired drop rate initially may well vary from this drop rate in time.

In an effort to provide greater accuracy of infusion rates, positive displacement infusion pumps have come into widespread use. Such pumps provide the advantage of accurately controlled infusion rates, largely independently of the pressure or the viscosity of the fluid being infused. However, such infusion pumps suffer from their own disadvantages. Because they typically operate at pressures of up to 60 psi, the danger of overpressure infusion is always present. Furthermore, infusion pumps tend to be relatively expensive, as well as heavy and cumbersome. In large part, the weight of infusion pumps is related to the size of the back up battery needed to power the pump in the event of a power failure. Because pumps operate motors on a regular basis, back up batteries for infusion pumps require large capacity.

The most basic part of control is to first obtain a precise volumetric measurement of the fluid administered.

U.S. Pat. No. 4,525,163 to Slavik et al teaches a flow control device including a sensor for measuring drop sizes. The drop sizes are measured as a calculation of averages after a certain number of optically detected drops fall into a burette. This is not a volumetric measurement and an additional drawback is that the administered fluid has to pass through the device, this being an invasive device.

U.S. Pat. No. 4,504,263 to Steur et al describes an invasive flow monitor where the flow of fluid passes through the monitor. The disadvantage of the invasive devices is that they have to be sterilized between uses and that becomes the responsibility and a resulting nuisance of the hospital requiring multiple devices with extras for sterilization. In the device described by Steuer the individual drops are measured by a infrared sensor. An additional drawback to the invasiveness of Steuer's invention is that he assumes that the drops are spherical which is not always the case.

There exist prior art describing non-invasive devices for counting drops such as described in U.S. Pat. No. 6,083,206 to Molko. Molko teaches a device that can count drops with great precision by sensing infra-red radiation passing through the drip chamber, but does not account for the volumetric measurement of each drop and must rely on the drop size designated by the particular set.

The necessity for volumetric precision becomes critical for tiny infants who receive even less than two milliliters of fluid administered in an IV drip per hour.

As infusion pumps and gravity fed intravenous sets have the abovementioned disadvantages it would be highly advantageous to have a simple gravity fed intravenous set devoid of the above limitations.

SUMMARY OF THE INVENTION

According to one aspect of the present invention there is provided a device for the volumetric measurement of a fluid administered in a gravity infusion set including a drip chamber. The device includes a housing configured for releasable deployment around a cylindrical surface of the drip chamber. The housing includes a source of radiation configured to emit radiation through the drip chamber in a path substantially perpendicular to an axis of the cylindrical surface and an optical receiver deployed to be adjacent to a portion of the cylindrical surface substantially opposite the source of radiation. The optical receiver is configured for quantitatively sensing the radiation and a processor operative to calculate a volume of each drop passing through the drip chamber as a function of the relative loss of radiation quantitatively sensed by the receiver during passing of a drop against a background radiation.

According to another aspect of the present invention there is provided a method for calculating a volume delivered through an intravenous set with a drip chamber configured for the flow of the fluid substantially along the drip chamber's axis. The method includes the steps of passing radiation from the exterior of the drip chamber through the drip chamber via a path generally perpendicular to the drip chamber axis to a sensor positioned on an opposite position on the exterior of the drip chamber, detecting and quantifying a background radiation value passing through the drip chamber, detecting and quantifying a radiation value passing through a drop falling through the drip chamber in order to obtain data indicative of a radiation loss due to the drop passing though the radiation path; and calculating a volume of the drop as a function of the relative loss of radiation detected during passing of the drop against the background radiation value.

According to yet another aspect of the present invention there is provided a method for calculating a volume delivered through an intravenous set with a drip chamber configured for the flow of the fluid substantially along the drip chamber's axis. The method comprises the steps of passing radiation from the exterior of the drip chamber through the drip chamber via a path generally perpendicular to the drip chamber axis to a sensor positioned on an opposite position on the exterior of the drip chamber, detecting and quantifying a background radiation value passing through the drip chamber, detecting and quantifying a radiation value passing through a drop falling through the drip chamber in order to obtain data indicative of a radiation loss due to the drop passing though the radiation path; and deriving a volume measurement for the drop using a lookup table, the lookup table formed by accumulating empirical data.

According to further features in preferred embodiments of the invention described below, the radiation is configured to function in pulsed mode.

According to still further features in the described preferred embodiments the radiation is configured to function in continuous mode.

According to further features in preferred embodiments of the invention described below, the radiation is light radiation.

According to still further features in the described preferred embodiments the radiation is infra-red radiation.

According to still further features in the described preferred embodiments a volume calculated is used for controlling the flow of a fluid administered in a gravity infusion set.

According to still further features in the described preferred embodiments a relative loss of radiation is converted into a volume with the aid of a lookup table. The lookup table is created by accumulating empirical data of drops passing through various infusion sets determining a relative loss of radiation during the passing of the drop through the radiation and then weighing the drops and determining the volume of each drop in proportion to its specific gravity. The device and method is suitable for use with any IV set and is non-invasive.

The present invention successfully addresses the shortcomings of the presently known configurations by providing a device and method for measuring the volume of a drop, which can be used to determine the volume of a fluid administered in a gravity infusion set.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 is an illustration of the radiation pulses before and after passing through a drip chamber, before and during the passage of a drop through the chamber.

DESCRIPTION OF THE PREFERRED EMBODIMENTS

Figure 1:
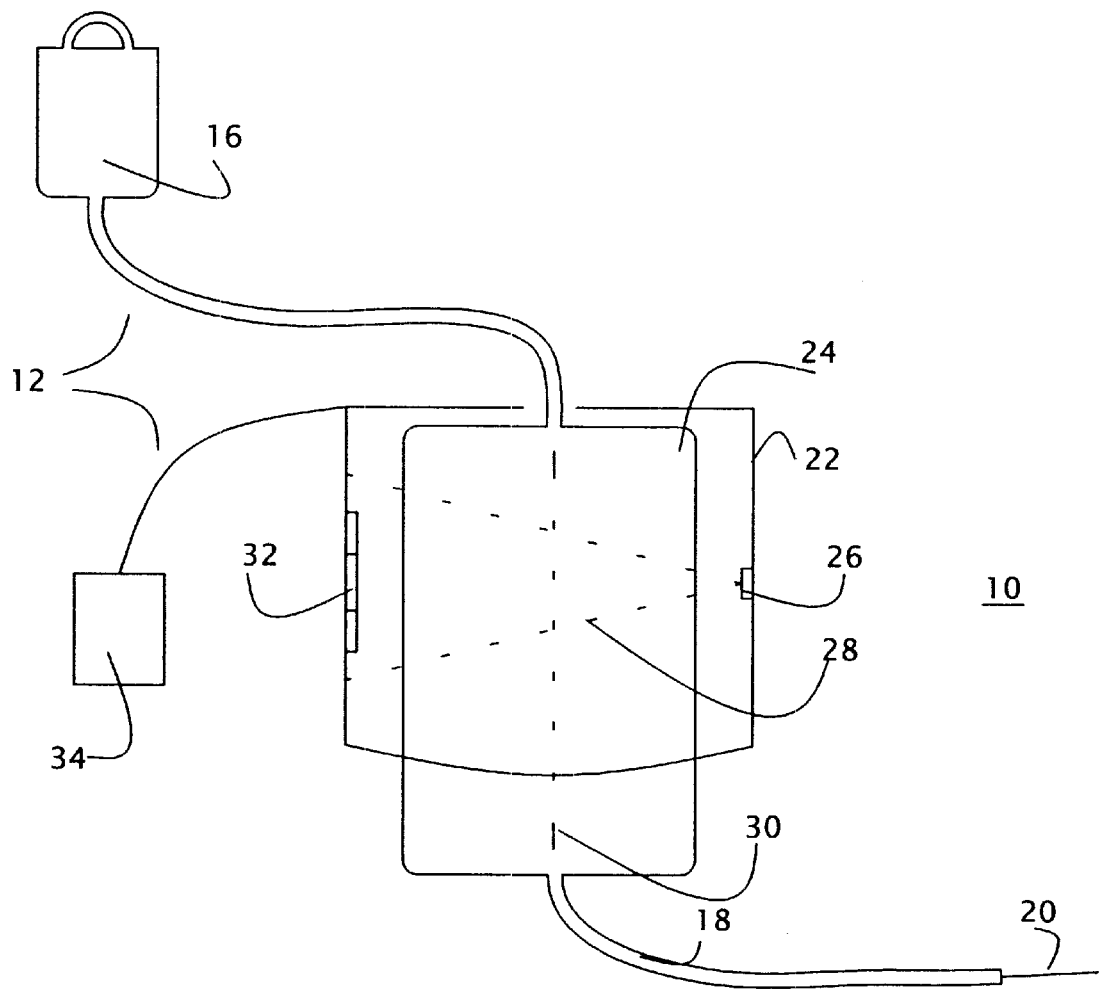
FIG. 1 is a device for the volumetric measurement of a fluid administered in a gravity infusion set.

The present invention is of a device and method for measuring the volume of a drop, which can be used to determine the volume of a fluid administered in a gravity infusion set.

Specifically, the present invention can be used to determine the volume of each drop administered in a gravity infusion set facilitating a most accurate knowledge of a total volume administered which can be used in the control of the flow of the fluid.

The principles and operation of a device and method for measuring the volume of a drop according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a device 10 for the volumetric measurement of a fluid administered in a gravity infusion set 12 including a drip chamber. Some of the parts are illustrated out of proportion in order to get a better understanding of the parts of the invention involved and how they combine with a gravity infusion set. Gravity infusion set 12 typically includes a reservoir 16, a drip chamber 14, a feed tube 18, and an IV needle 20.

Device 10 includes a housing 22 configured for releasable deployment around a cylindrical surface 24 of drip chamber 14. Housing 22 fits over drip chamber 14 and is attached to any of a number of places including the tube leading into drip chamber 14 or alternately to the top portion of drip chamber 14 or to the stand supporting set 12. Housing 22 includes a source of radiation 26. Source of radiation 26 is configured to emit radiation 28 through drip chamber 14 in a path substantially perpendicular to an axis 30 of cylindrical surface 24. An optical receiver 32 configured for quantitatively sensing radiation is deployed to be adjacent to a portion of cylindrical surface 24 substantially opposite source of radiation 26.

Preferably the radiation from a source of radiation 26 emitted is infrared light. Alternately or additionally other types of radiation could be used as well. Source of radiation 26 includes an array of infrared light emitting diodes that generate infrared light. According to the present invention the infrared radiation is emitted either in a continuous mode or alternately in a pulsed mode.

Among the advantages of a pulsed mode are improved control in accounting for background radiation level and in saving energy. A preferable pulse rate is a rate of thousands of pulses and preferably at approximately 100,000 pulses per second. Pulsed mode is helpful in prevention of disturbances in background radiation measurements for example when light from an external source such as sunlight shines onto the drip chamber.

A pulser in source of radiation 26 periodically energizes the light emitting diodes to produce a series of energized and non-energized states. FIG. 2 illustrates the difference between pulses of radiation detected and quantified by optical receiver 32 after having passed through drip chamber 14 with no drop (FIG. 2a) in the path of the radiation and with a drop 40 (FIG. 2b) in the path of the radiation.

FIG. 2a illustrates pulses of radiation 14 represented digitally. An Analog-to-Digital converter is used to convert radiation pulses into digital code, a measurable voltage or some other measurable electrical reaction to the analog signal. Pulses 40 passing through drip chamber 14 when no drop is in the path of the radiation are measured and there is no significant variation in height between the pulses measured by optical receiver 32 passing through chamber 14. There is of course a difference between the radiation going in to chamber 14 and detected by optical receiver 32 on the other side of chamber 14. This is the background or reference level. Device preferably 10 calibrates itself before and after each drop passing through drip chamber 14 which takes into account any changes in the environment inside or outside. Examples of changes that need to be taken accounted for are foggy-like droplets formed on the outside of chamber 14 or tiny droplets splashed on the inside surface of chamber 14. As device 10 is suitable for any gravity IV set 12, there are inherent differences between various drip chambers, such as wall thickness or wall constitution. A processor 34 controls the energizing of the infrared emitting diodes in accordance to the radiation sensed on the other side of chamber 14 and adjusts the radiation for each set and continues to calibrate itself many times between each drop.

FIG. 2b illustrates a drop 42 passing through chamber 14 and the resultant decrease in radiation passing through chamber 14. A dip 44 in radiation sensed by sensor 32 is illustrated, wherein the minimum signal 46 in dip 44 corresponds to the thickest segment diameter of drop 42 passing through chamber 14. FIG. 2b illustrates the significance of preferably having many tens of thousands of pulses per second, which means that a few hundred pulses would pass through each drop 42 passing through drip chamber 14. Accuracy of device 10 in the volumetric measurement of a drop increases with the amount of pulses passing through a drop. Each pulse represents a segment of a drop so more pulses passing through a drop give a more accurate final result which is the volume of the drop. Device 10 calculates the volume of a drop regardless of the shape of the drop or the type of IV set. A drop may be elongated or alternately a relatively wide and flat drop. Many factors influence the shape of the drop including pressure, the width of the entrance into the drip chamber, the fluid viscosity and whether the entrance to the drip chamber is perfectly round or not.

Processor 34 is operative to calculate a volume of each drop 42 passing through drip chamber 14 as a function of the relative loss of radiation quantitatively sensed by receiver 32 during passing of drop 42 against a background or reference level of radiation.

In order to be able to calculate a volume for each drop, a lookup table is first formed by accumulating empirical data. Empirical data is obtained by running device 10 with numerous sets, each set with its own drop types. Each drop has its own dip in radiation passing through. Each drop is then weighed on an analytical balance to produce a precise weight. Taking into account the specific gravity for each type of fluid, a volume for each can be easily calculated. For example with water 1 kilogram water occupies a volume of one liter. Various specific gravities of fluids will have corresponding volumes slightly different than that of water. This procedure is repeated many times, preferably thousands of times, such that it is possible to relate a weight and therefore a volume to a dip or an integral which is the value that is related to the dip.

Infrared light emitted in continuous mode is be more precise than pulsed mode as the information missing between the pulsed will be provided, and the drawback of sunshine or other light interfering with the infrared can be overcome by making housing 22 non transmitting to light from the outside, much like a black box. A significant drawback is the high demand for power for a continuous flow of radiation. In many cases where the preferable power supply to device 10 is a battery powered supply which enables easy mobility from one patient to another, a continuous mode of radiation supply would deplete the batteries rapidly. Alternatively, in another embodiment of the present invention, device 10 is powered by AC current, and preferably has a source of batteries for backup in which case continuous mode would be the preferred mode. This would be particularly advantageous for a permanently positioned device 10 or when more precision is required.

Figure 3:
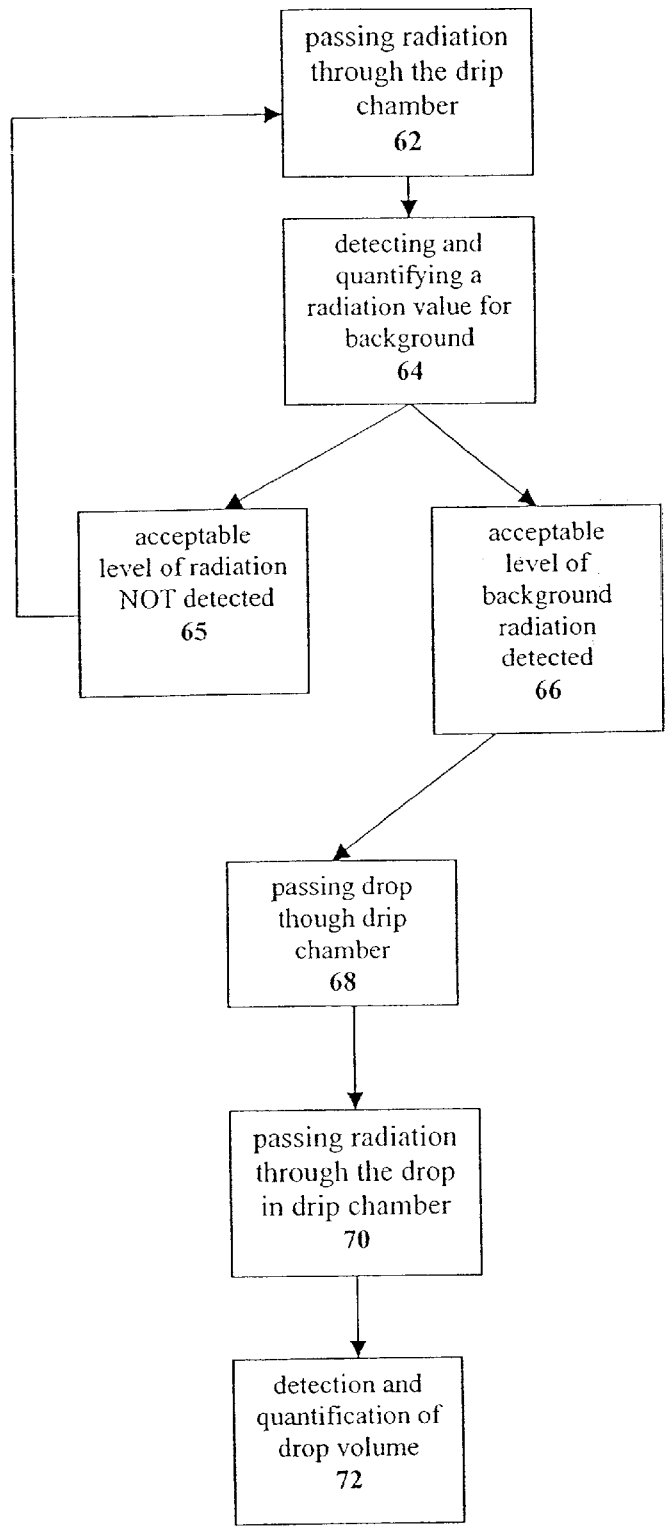
FIG. 3 is a flow chart of a method for calculating the volume of a drop.

Reference is now made to FIG. 3 which is a flow diagram of a method 60 for calculating a volume delivered through an intravenous set with a drip chamber configured for the flow of the fluid substantially along the drip chamber's axis. Method 60 includes the steps of passing radiation 62 from the exterior of the drip chamber through the drip chamber via a path generally perpendicular to the drip chamber axis to a sensor positioned on an opposite position on the exterior of the drip chamber and detecting and quantifying 64 a background radiation value passing through the drip chamber. If the background radiation value was either too low or too high 65, then the amount of radiation to be passed through chamber 14 is modified to a higher or lower radiation and is passed through again 62. This stage is repeated until a predetermined level of radiation is reached. This could depend on many factors, such as set type and formation of frost on the chamber. Once a predetermined level of radiation has been reached, it is possible to calculate the volume of a drop. The next step occurs when a drop passes through the chamber 68. Radiation preferably in the form of infrared light is passed through a drop falling through the drip chamber 70. The sensor detects and quantifies the radiation 72 in order to obtain data indicative of a radiation loss due to the drop passing though the radiation path. The volume of the drop is then calculated as a function of the relative loss of radiation detected during passing of the drop against the background radiation value. The volume calculated for a drop is used in the control of fluid administered making control more precise.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for calculating a volume delivered through an intravenous set with a drip chamber configured for the flow of the fluid substantially along the drip chamber's axis, method comprising the steps of:

(a) passing radiation from the exterior of the drip chamber through the drip chamber via a path generally perpendicular to the drip chamber axis to a sensor positioned on an opposite position on the exterior of the drip chamber;

(b) detecting and quantifying a background radiation value passing through the drip chamber;

(c) detecting and quantifying a radiation value passing through a drop falling through the drip chamber in order to obtain data indicative of a radiation loss due to said drop passing though said radiation path; and (d) deriving a volume measurement for said drop using a lookup table, said lookup table formed by accumulating empirical data.

2. The method of claim 1, wherein said radiation is configured to function in pulsed mode.

3. The method of claim 1, wherein said radiation is configured to function in continuous mode.

4. The method of claim 1, wherein said radiation is light radiation.

5. The method of claim 1, wherein said radiation is infrared radiation.

6. The method of claim 1, further comprising the step of controlling the flow of a fluid administered in a gravity infusion set using the volume calculated for a drop.

7. The method of claim 1, wherein said empirical data is accumulated by weighing a plurality of drops passed through said radiation path and determining the volume of each drop in proportion to its specific gravity.

* * * * *